(12) United States Patent
Pienkowski et al.

(10) Patent No.: US 6,872,403 B2
(45) Date of Patent: Mar. 29, 2005

(54) POLYMETHYLMETHACRYLATE AUGMENTED WITH CARBON NANOTUBES

(75) Inventors: David A. Pienkowski, Lexington, KY (US); Rodney J. Andrews, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 89 days.

(21) Appl. No.: 09/773,293

(22) Filed: Jan. 31, 2001

(65) Prior Publication Data

US 2002/0001620 A1 Jan. 3, 2002

Related U.S. Application Data

(60) Provisional application No. 60/179,569, filed on Feb. 1, 2000.

(51) Int. Cl.[7] ................................. A61F 13/00
(52) U.S. Cl. ..................... 424/422; 424/400; 424/486; 424/487
(58) Field of Search ................ 424/422, 400, 424/486, 487, 489; 343/840; 422/44

(56) References Cited

U.S. PATENT DOCUMENTS

| | | | |
|---|---|---|---|
| 4,064,566 A | * | 12/1977 | Fletcher et al. ............... 3/1.9 |
| 4,330,283 A | | 5/1982 | Michl et al. |
| 4,693,986 A | | 9/1987 | Vit et al. |
| 4,963,151 A | | 10/1990 | Ducheyne et al. |
| 5,021,063 A | | 6/1991 | Tager |
| 5,030,238 A | | 7/1991 | Nieder et al. |
| 5,049,157 A | | 9/1991 | Mittelmeier et al. |
| 5,108,452 A | | 4/1992 | Fallin |
| 5,171,560 A | * | 12/1992 | Tennent ...................... 423/447 |
| 5,180,394 A | | 1/1993 | Davidson |
| 5,266,609 A | | 11/1993 | Hall et al. |
| 5,334,625 A | | 8/1994 | Ibsen et al. |
| 5,336,699 A | * | 8/1994 | Cooke et al. ................ 523/115 |
| 5,686,182 A | | 11/1997 | Maniar |
| 6,027,742 A | * | 2/2000 | Lee et al. .................... 424/422 |
| 6,099,960 A | * | 8/2000 | Tennent et al. ............. 428/367 |
| 6,280,759 B1 | * | 8/2001 | Price et al. ................. 424/408 |
| 6,284,832 B1 | | 9/2001 | Foulger et al. |

\* cited by examiner

*Primary Examiner*—Thurman K. Page
*Assistant Examiner*—R. Berko
(74) *Attorney, Agent, or Firm*—King & Schickli, PLLC

(57) ABSTRACT

An augmented synthetic resin is provided. That resin includes carbon nanotubes dispersed in a polymethylmethacrylate matrix. The method of preparing this synthetic resin includes the mixing and disaggregating of the carbon nanotubes.

15 Claims, No Drawings

POLYMETHYLMETHACRYLATE AUGMENTED WITH CARBON NANOTUBES

This application claims the benefit of U.S. Provisional Application No. 60/179,569 filed Feb. 1, 2000.

This invention was made with partial government support from the NSF under MRSEC DMR9809686 and, accordingly, the government may have certain rights in the invention.

TECHNICAL FIELD

The present invention relates generally to an augmented polymethylmethacrylate suitable for use in medicine or dentistry as a bone cement, dental restoration or other type of medical or dental prosthesis.

BACKGROUND OF THE INVENTION

Each year over 500,000 human joints require replacement as a result of debilitating disease or traumatic injury. Hip and knee joints represent a majority of these cases. To meet this need, a large number of partial and total joint orthopedic implants have been designed and are presently being marketed by various manufacturers. These devices are some of the most remarkable surgical developments of the $20^{th}$ century because they dramatically restore pain-free mobility to diseased, worn, or traumatized joints and thereby prevent joint dysfunction from limiting the quality and quantity of life. Examples illustrative of the types of orthopedic implants available include but certainly are not remotely limited to U.S. Pat. No. 5,020,063 to Tager, U.S. Pat. No. 5,030,238 to Nieder et al., U.S. Pat. No. 5,108,452 to Fallin and U.S. Pat. No. 5,180,394 to Davidson.

Total joint prostheses are secured to the host bone utilizing one of two different techniques, bone ingrowth into specially engineered and manufactured pores on the surface of the implant, or bone cement. Porous ingrowth fixation methods have three limitations. First, implant fixation by porous ingrowth requires a period of post-operative restricted weight bearing. Delays in post-operative ambulation can have adverse clinical consequences on the respiratory system and overall health of older patients. These generally lead to additional costs from prolonged post-operative hospitalization. Second, in the event of infection or excessive bearing surface wear, porous ingrowth total joint implants are difficult to remove (revise) and frequently require fracture of the bone cortex. Finally, there always exists the potential for early failure due to an inability to achieve adequate ingrowth. This means lack of fixation and failure of the prosthesis. When bone ingrowth does not occur, revision joint surgery becomes necessary.

Bone cement is the common name given to polymethylmethacrylate polymer that in its medical (orthopedic) grade is used as the load-transferring material between a total joint prosthesis and the bone implantation site. Commercially available bone cement is a two-phase material that consists of a liquid methylmethacrylate monomer and a fine pre-polymerized polymethylmethacrylate powder. These components are packaged separately, mixed together in the operating room in a vacuum-mixing chamber and inserted under pressure into the prepared bone cavity before the polymerization reaction is complete. The liquid monomer contains a promoter or accelerator (to initiate the free-radical reaction) and a stabilizer (to prolong shelf-life) and the powder contains an initiator (a catalyst) and a radiopacifier. Radiopaque material is commonly added to bone cement to enable the radiologist to "see" the cement mantle, monitor its integrity and observe the presence of defects.

The name "bone cement" is actually a misnomer because instead of serving as an adhesive, it more accurately serves as a grout or interfacial material between the reamed medullary canal of the proximal femur or tibia for total hip or knee implants, respectively, and the metallic stem of the prosthesis. Bone cement applied to the medullary canal is intended to form a layer (mantle) of uniform thickness between the bone and the implant stem. This cement mantle is intended to mechanically interlock with the pores of the prepared bone and structurally compensate for the inability of the surgical technique to create a cavity in bone that exactly matches the shape of the total joint stem.

Bone cement is the technology of choice for older patients because it virtually guarantees secure, immediate post-operative implant fixation and allows patients to ambulate soon after surgical implantation of the new joint. This avoids respiratory complications, reduces post-operative morbidity and mortality and reduces the duration of hospitalization and rehabilitation. This is particularly important because two-thirds of all hip replacement patients are older than 65 years of age. Total joint prostheses used for cemented fixation are also less expensive than implants used for porous ingrowth fixation and they also have smaller surface areas and thus less likelihood of releasing metal ions into the body. They are also easier to revise in the event of joint bearing surface failure or infection.

Active or overweight total joint patients with cemented implants frequently experience failure of the cement mantle. This occurs in approximately 5% of all such patients about 10 years post-operative. In fact, failure rates as high as 67% after 16 years in patients younger than 45 years old have been documented. Failure of the cement mantle results in loss of fixation, subsidence and motion of the implant in the medullary canal, pain on ambulation, and ultimately, failure of the implant.

Mechanical fatigue fracture of the cement mantle is believed to be one of the chief causes of bone cement failure. Fatigue failure of bone cement is believed to occur in three phases. In the first phase the crack initiates, generally from a flaw in the material's continuity. In the second phase the crack slowly propagates. In the third phase the crack propagates rapidly to failure.

Although recently developed cementing techniques have helped prolong the life of bone cement by eliminating air bubbles in the cement and thereby eliminating this source of stress risers, attempts to augment the mechanical properties of bone cement by the additional of various other materials have generally met with failure. Specifically, stainless steel fibers, polymethylmethacrylate fibers, long macroscopic carbon fibers, polyethylene fibers, aramid fibers and titanium mesh have all been added to bone cement in attempts to bridge bone cement cracks and arrest propagation at stage two. These attempts have been unsuccessful for a variety of reasons including, particularly, the adverse effect such materials have on the mixing of polymethylmethacrylate, the increase in viscosity and the poor fiber/material bonding with the polymethylmethacrylate matrix.

While the prior art teaches that carbon fibers of average length less than 0.1 mm do not provide a desired reinforcing effect in polymethylmethacrylate based resins (note U.S. Pat. No. 4,064,566 to Fletcher et al.), we have now found that carbon nanotubes provide substantially enhanced load bearing mechanical properties to polymethylmethacrylate resins and thereby extend the in vitro service life of polymethylmethacrylate bone cements.

Additionally, carbon nanotube augmented polymethylmethacrylate resins provide improved strength to dental prostheses (e.g. false teeth) to better withstand the forces which are produced in the oral cavity when chewing. Thus, the carbon nanotube augmented polymethylmethacrylate resins provide an excellent material from which one may construct alone or in combination with other compounds dental restorations including but not limited to; dentures, crowns, bridges and other prostheses.

SUMMARY OF THE INVENTION

The present invention relates to a synthetic resin comprising a polymethylmethacrylate matrix augmented with carbon nanotubes. The resin may be utilized as a bone cement for joint prosthesis, dental prosthesis and/or dental restoration fixation in bone tissue. The resin may also be used in the production of prostheses and restorations including, for example, dental crowns, bridges, teeth and other prostheses.

The carbon nanotubes are provided at a weight percentage of between substantially 0.005–5.0 and more typically 0.15–2.0. The carbon nanotubes have diameters between substantially 10–50 nanometers and lengths between substantially 10–1000 nanometers. Either single-walled or multi-walled carbon nanotubes may be utilized although for many applications, multi-walled carbon nanotubes exhibit more beneficial characteristics.

In accordance with still another aspect of the present invention, the hollow spaces in the carbon nanotubes may be loaded to carry minute quantities of pharmaceutically beneficial compositions. Such compositions may be selected from a group consisting of antibiotics, anti-inflammatories, chemotherapeutic agents, bone growth promoting agents and any mixtures thereof.

The carbon nanotube augmented polymethylmethacrylate resin of the present invention provides substantially enhanced mechanical properties. Advantageously, the presence of carbon nanotubes dispersed in the polymethylmethacrylate resin inhibits shrinkage of the resin as it cures thereby promoting better bone-implant or denture fit and load transfer between the implant and bone or prosthesis and oral cavity. Carbon nanotubes are also thermally and electrically conductive and could also have a role as a heat transferring and an electrode-promoting material which acts as a component of a temperature sink or bone growth stimulation system.

Still other benefits and advantages of the present invention will become readily apparent to those skilled in this art from the following description wherein there is shown and described a preferred embodiment of this invention simply by way of illustration of one of the modes best suited to carry out the invention. As it will be realized, the invention is capable of other different embodiments and its several details are capable of modification in various, obvious aspects all without department from the invention. Accordingly, the drawings and descriptions will be regarded as illustrative in nature and not as restrictive.

DETAILED DESCRIPTION OF THE INVENTION

As noted above, the present invention relates generally to an augmented synthetic resin comprising carbon nanotubes dispersed in a biocompatible polymethylmethacrylate matrix (i.e. a biocompatible polymer of polymethylmethacrylate dissolved in a biocompatible reactive monomer of methylmethacrylate). Of course, the resin may also include or incorporate any appropriate inhibitor, promoter or accelerator, stabilizer, initiator, catalyst, radiopacifier and/or radiopaquing agent of a type known in the art.

The augmented synthetic resin is particularly suitable for use in medicine or dentistry and is characterized by a unique set of chemical, physical, and electrical properties that are particularly adapted for (1) application as a bone cement for joint prosthesis, material for dental prosthesis and/or dental restoration fixation in bone tissue; (2) use in the production of prostheses and restorations including, for example, dental crowns, bridges, teeth, etc.; or (3) use as bone growth stimulation electrodes in medical or dental prostheses.

The carbon nanotubes are provided in the resin at a weight percentage of between substantially 0.005–5.0 and more typically 0.15–2.0. The carbon nanotubes generally have diameters ranging between substantially 10–50 nanometers and lengths between substantially 10–1000 nanometers. Either single walled or multi-walled carbon nanotubes may be utilized. The advantageous properties of such carbon nanotubes are realized so long as the nanotubes are thoroughly disaggregated and uniformly dispersed throughout the resin material.

The desired carbon nanotubes disaggregation and dispersion may be achieved in a number of ways. The first and most preferred technique useful for this purpose is ultrasonic agitation. In this approach, the tip of a sonic dismembranator, that is an ultrasonic probe used to disrupt cell membranes, is inserted into a mixture of the carbon nanotubes and the liquid methylmethacrylate monomer. Power levels of between 175–475 watts and preferably above 200 watts are utilized for a total of between 10–60 minutes to complete the disaggregation and dispersion of the nanotubes in the monomer. After the specified period of ultrasonic agitation is completed, the probe is removed and the monomer containing nanotubes is vacuum mixed with the biocompatible polymer of polymethylmethacrylate. Following mixing, the polymerizing "dough" is injected into the medullary canal where it will polymerize in vivo in order to hold a prosthesis or implant in place in the bone. Alternatively, the mixed augmented synthetic resin may be injected into a dental restoration or other mold alone or in combination with other appropriate materials where it may polymerize in the shape of a crown, plate, bridge or other appropriate dental restoration.

In a second possible disaggregation and dispersement technique, the appropriate amount of carbon nanotubes are added to a small quantity (e.g. 10 ml) of reagent grade ethanol. The ultrasonic probe is then inserted into the ethanol-nanotube solution and ultrasonic agitation is used to disaggregate and disperse the nanotubes for a period of time as described above. Next the ethanol-nanotube solution is mixed with an appropriate amount of the polymethylmethacrylate polymer, applied to a clean glass surface and the ethanol component is removed, for example, by heating in a vacuum oven to 37° C. for 48 hours. After equilibrating to room temperature the nanotube/powder mixture is removed from the oven and vacuum mixed with the appropriate amount of biocompatible methylmethacrylate monomer. After an appropriate mixing-curing time, the bone cement is then ready for injection.

In a third approach, the carbon nanotubes are added to a selected quantity of ethanol and an appropriate amount of methylmethacrylate monomer before being subjected to ultrasonic agitation. Once the nanotubes are thoroughly distributed in the ethanol and monomer mixture, as detected by uniformity of coloration, the ethanol is removed by fractionation. The monomer liquid containing the dispersed nanotubes, but no ethanol, is then vacuum mixed with the polymethylmethacrylate polymer and readied for injection.

In still another technique, shatter milling is utilized. Shatter milling is a multi-body cryogenic mechanical technique that derives its name from the disruptive mechanical action of two steel balls contained in a small sealed steel container that is subjected to repetitive agitation. Shatter milling begins by opening a threaded steel end cap of this container and then removing one of the two steel balls. The appropriate amount of carbon nanotubes, polymethylmethacrylate polymer powder and liquid nitrogen (approximately 20% of maximum capacity) are added to the container. The second steel ball is reinserted in the container and the steel end cap is replaced. The sealed container is then placed in a motorized shaking apparatus which moves the container rapidly back and forth in a 3D arc motion which causes the two steel balls to shatter the powder contents against each other and against the sides of the container. This serves to disaggregate the nanotubes and disperse them throughout the polymethylmethacrylate polymer powder. Following "shattering" the material is removed from the container, the nanotubes-polymethylmethacrylate is vacuum mixed with the appropriate amount of methylmethacrylate monomer (the liquid nitrogen component boils away) and readied for injection.

Yet another possible method for disaggregation/dispersion employs the principles of particle shear which is induced by passing a pressurized stream of solvent containing carbon nanotubes through an expansion nozzle. As the carbon nanotubes are passed through the nozzle, the shearing forces within the fluid cause the nanotubes to separate and disperse into the liquid stream. Of course, the disaggregation and dispersion techniques recited above should be considered as illustrative of the various approaches available to achieve the desired end and not as restrictive.

The multi-walled carbon nanotubes are made from rolled graphene sheets that are capped with hemispheres similar to $C_{60}$ to form hollow multi-walled tubular structures. The carbon nanotubes utilized have tensile strengths that are up to 4000 times stronger than steel (at only one-sixth the weight) and as much as 200 times stronger than carbon fibers. The carbon nanotubes are also flexible, thermally and electrically conducting, and have magnetic properties. The carbon nanotubes also have a surface area to volume ratio that is up to six orders of magnitude larger than an equivalent volume of carbon fibers. The multi-walled carbon nanotubes not only have a very high length/diameter ratio but also a large surface area per volume. Carbon nanotubes bond to carbon-based matrices like polymethylmethacrylate polymer by comparatively weak van der Waals bonds. Even though individual van der Waals bonds are comparatively weak, there are so many more of them per mass of carbon nanotubes than per unit mass of carbon fiber, the carbon nanotube-polymethylmethacrylate matrix adhesion strength is very large such that the bond strength is greater and the mechanical fatigue strength and compression strength are enhanced.

Further, unlike the comparatively macroscopic size of previously used reinforcing fibers/particles, carbon nanotubes are much smaller and this size difference aids in the uniform distribution and orientation of the carbon nanotubes throughout the polymethylmethacrylate resin. The resulting large numbers of well dispersed carbon nanotubes suggest that they are more likely to be at the site which bridges a freshly nucleated crack in position to resist or prevent crack propagation. The random orientation of the carbon nanotubes means that many will have their longitudinal axis perpendicular to the crack. Together, the spatial orientation, strong nanotube-matrix bonding, extremely strong tensile properties and flexibility in conjunction with their widespread numerous distribution indicate their theoretical effectiveness in arresting crack propagation and growth. Thus, the carbon nanotubes effectively extend the longevity of the cement mantle.

The augmented synthetic resin of the present invention provides a number of advantages and benefits. The carbon nanotubes inhibit shrinkage of the resin as it cures and thereby promotes a better bone-implant fit, better load transfer and better clinical performance. The high heat conductivity of nanotubes may also help to prevent polymerization induced thermal necrosis of bone that otherwise results from the high temperatures that occur during in vivo polymerization of the synthetic resin used in the medullary canal between the implant and the bone. Specifically, the carbon nanotubes help prevent local polymerization hyperthermia-induced destruction of the bone tissue adjacent to the cement mantle. This is because carbon nanotubes have an extremely high on-axis thermal conductivity second only to diamond. Thus, the carbon nanotubes conduct the heat of polymerization to the large metallic stem of the implant which effectively functions as a heat sink. This conduction also functions to eliminate localized "hot" spots of polymerization heat in the cement mantle of the type that may be responsible for highly localized areas of bone lesions such as have been observed radiographically in the past when many prior art bone cements are utilized.

It is also hypothesized that the nanotubes will help prevent chemically induced bone necrosis. Specifically, unreacted monomer has a tendency to leach from the cement mantle and is thought to be a factor contributing to chemical necrosis of bone. This is a significant problem because the escaping monomer comes in intimate contact with the bone at the critical cement mantle interface. Chemical mediated destruction of this bone at the interface may lead to stress concentrations and failure of the cement mantle. Advantageously, the high affinity of carbon nanotubes for such monomer will allow the nanotubes to act as scavaging agents and prevent the leakage of potentially detrimental monomer.

Still further, the carbon nanotubes conduct electricity either by metallic induction or by one of two semiconductor mechanisms. The electric conductive properties of the carbon nanotubes could serve as electrodes or electrical conduit materials in medical or dental prostheses that use electrical stimulation. This would enhance the effectiveness and clinical convenience of electric bone growth stimulators resulting in improved bone growth in and around the implant. This, of course, enhances the mechanical strength of the mounting of the implant in the bone. To achieve this end, locally high concentrations of carbon nanotubes could be provided in the methylmethacrylate matrix at selected points, regions or zones along the cement mantle or prosthesis as desired to promote the necessary bone growth.

Since iron-based catalysts such as ferrocene are used in the production of carbon nanotubes, the nanotubes exhibit magnetic properties. Thus, by application of external magnetic fields to the still polymerizing synthetic resin, it is possible to selectively orient and redistribute nanotubes prior to curing and thereby confer a preferred alignment thereof to better resist failure in a given direction (e.g. to better withstand tensile forces in a given direction). This technique may also be used to position drug loaded nanotubes in greater concentrations along the bone/cement mantle interface.

The carbon nanotubes also simplify bone cement application. The added strength and improved mechanical properties imparted to the resin by the carbon nanotubes allow a wider range of cement mantle thickness to provide the necessary/desired characteristics to properly maintain the prosthesis in the bone. Additionally, the carbon nanotubes darken the bone cement providing greater visual contrast which aids intra-operative visual identification of bone cement location. This facilitates complete removal of the cement from the bone in the event revision surgery ever becomes necessary due to infection, excessive joint bearing wear or aseptic loosening.

Still further, infection of an implant is considered a devastating complication and treatment options remain controversial and are often ineffective. Advantageously, carbon nanotubes include hollow spaces therein capable of carrying minute quantities of pharmaceutically beneficial compositions. Such compositions may, for example, be selected from a group consisting of small sized antibiotics, anti-inflammatories, chemotherapeutic agents, bone growth promoting agents and any mixtures thereof. The loading of the hollow spaces in the nanotubes with appropriately sized antibiotic drugs or other agents to treat infection should function at the site as a prophylactic to address this problem. Bone growth promoters as well as other desired proteins and agents function to provide site effective measures to enhance the bonding of the implant to the surrounding bone.

The following examples are presented to further illustrate the invention, but it is not to be considered as limited thereto.

EXAMPLE 1

Carbon nanotubes are first scraped from the quartz substrate upon which they are grown. An appropriate quantity (to the intended percentage desired in a preplanned amount of cured medical or dental grade polymethyl-methacrylate (PMMA)) of nanotubes is then weighted by using a precision balance. These nanotubes are then added to a solution of methyl-methacrylate monomer. The amount of this monomer is typically one-half of the total amount of monomer to be used in preparing the preplanned amount of PMMA. This 50% amount of monomer is placed into a beaker and then the previously mentioned precision weighted amount of nanotubes is added to this monomer. The beaker with monomer and nanotubes is then placed into another much larger beaker to which many ice particles have been added. When the monomer mixture is cooled to 0 degrees C or less, the probe of an ultrasonic dismembranator is inserted into the liquid. This probe is positioned carefully so as to be fully immersed, yet be more than 8 mm or so from the bottom of the beaker. The ultrasonic probe is set to a power level of (typically) 200 Watts, and turned on for 30 seconds. At the end of this time, the probe is turned off for 30 seconds and the mixture is allowed to cool. This cycle of 30 seconds on/30 seconds off is repeated for a total on time of between 5 minutes to 60 minutes (depending upon nanotube concentration and probe power level). Proper disaggregation and dispersion of the nanotubes is preliminarily confirmed by visual appearance of the solution (uniform coloration) and verified by preparation into a polymer (after mixing with additional monomer, polymer, curing) and then freeze fracture and scanning electron microscopic analysis of the freeze fractured surface.

Once all ultrasonic agitation of the nanotube containing initial amount of monomer has been accomplished, the monomer is then mixed with the remaining amount of monomer and then inserted into the mixing chamber along with the appropriate amount (usually twice the weight of monomer) of prepolymerized polymethylmethacrylate powder. If the mixture is intended for medical applications, e.g., bone cement, said mixing is done in a vacuum (typically ½ to 1 atmosphere). If the mixture is intended for dental applications, said mixing might occur without a vacuum.

If this mixture is intended to also serve as a scaffold for electrical simulating device to enhance long bone or oral bone growth, then another parallel nanotube disaggregation and dispersion effort will be performed, but with a larger concentration of same or slightly different size/catalyst/ number of walls, etc. nanotubes. This later mixture will have much higher electrical conductivity (in the cured state) and will serve as electrical conduits or as electrodes making direct contact with bones such as the tibia, femur, or mandible or maxilla, etc. At the appropriate stage of curing of the first mixture (low nanotube concentration of PMMA designed to optimize certain mechanical properties such as fatigue resistance or bending resistance), the second concentration of nanotubes may be added to incorporate the electrically conducting features of the final PMMA medical or dental device. At this time, other elements of the circuit (connections, batteries, constant current regulating circuitry, etc.) may also be added.

This curing mixture of one or two concentrations of nanotubes will then be shaped by its container or by alternative means to produce the desired medical or dental device.

If carbon nanotubes can successfully augment the mechanical properties of denture based acrylic, it would suggest that dental prostheses would be able to endure more or higher amplitude (or both) stress cycles. This would simplify the use of denture based acrylic by eliminating the need for metal reinforcement in certain high stress locations for certain patients. Currently, cast metal may need to be incorporated into dental prostheses in thin areas to reduce the chance of breakage. With successfully augmented dental acrylic this additional procedure and its expense would be eliminated.

Sample Preparation and Mechanical Testing

We have conducted preliminary tests on carbon nanotube augmentation by using research grade polymethylmethacrylate as the matrix. Carbon nanotubes are first scraped from the surface on which they are grown by using a single-edge razor blade. These nanotubes are then placed in a vial for future weighing. For each batch of augmented dental acrylic, ten grams of liquid methylmethacrylate monomer are weighed by using a precision electronic balance. This monomer is then placed in a beaker and inserted into another larger beaker containing crushed ice (to cool the monomer and prevent its evaporation). To this liquid monomer are added a small amount of multiwalled carbon nanotubes (MWNT). These nanotubes weigh between $\frac{1}{16}$ to ½ of 1%, to as much as 2% of the total amount of acrylic (30 g, 10 g of monomer plus 20 g of polymer). A key step following this addition is that the carbon nanotubes must first be disaggregated and then uniformly dispersed (both location and orientation) throughout the liquid monomer. Disaggregation is needed because of the tendency for carbon nanotubes to firmly adhere to each other in a parallel axis arrangement. [Smalley, 1999] (FIG. 1) This behavior is analogous to the tendency for long pasta noodles to axially align and stick together in a bowl shortly after cooking. Nanotube aggregation originates with the method of production (growth of nanotubes at right angles on a substrate) and the removal (scraping) of these nanotubes from the substrate by using a razor blade.

Uniform dispersion of the nanotubes in the PMMA is as critical in this study as in every other study [Lewis, 1997] [Quin, 1999] except that the small size of the nanotubes confers an enormous advantage over prior uses of comparatively macroscopic fibers and meshes. Dispersion of the disaggregated nanotubes in the monomer component is accomplished by a process developed in our laboratory. The tip of an ultrasonic cell dismembranator is inserted into the cooled monomer (with nanotubes added) and turned on to 50% of maximum (typically, 200 Watts) power. The sonic dismembranator operates for 10 seconds, and is then turned off for 10 seconds. This process, i.e., a 50% on-time (duty cycle) is repeated for a total of 60 minutes (total of 30 minutes on time).

After this time, the cooled monomer containing the disaggregated and dispersed nanotubes is then poured into a mixing bowl to which was previously added twenty grams of polymerized polymethylmethacrylate powder (previously weighed (to 0.01 g) on the precision electronic balance). This mixing process occurs over a carefully controlled 3-minute duration in a vacuum (½ atmosphere) mixing bowl (to minimize air bubbles in the mixture). The entire process is also done in a fume hood to minimize airborne odors. As soon as the monomer and polymer are thoroughly mixed, the mixture is then poured and scooped with a spatula into a bone cement gun cartridge, and then this mixture is squirted at high pressure into either a pre-prepared silicone mold for tensile test specimens, or an open-faced stainless steel mold used for bending specimens. The specimens are allowed to air cure in the molds at room temperature in the fume hood for 24 hours, after which time they are removed from the molds and allowed to cure in air for 1 week in the fume hood at room temperature.

At the end of this 1-week curing period, the specimens were inserted into the jaws of a custom-built tensile specimen test fixture (made according to ASTM draft specifications) and tested to failure at an actuator displacement rate of 2.54 cm per second. The results of these tensile testing studies have shown that the control (0% nanotube concentration) specimens withstood a mean maximum tensile stresses of 38 Mpa,±7.7 Mpa std. Dev, n=12), and this value compares favorably with the values measured by others. ([Lewis, 1997]) the addition of carbon nanotubes in preliminary testing (Table 1) has shown that the small fractions of one percent of carbon nanotubes in research grade polymethylmethacrylate can enhance the tensile strength and stiffness of this material by as much as 78% and 91% respectively.

TABLE 1

| Nanotube concen. | 0 (control) | ⅛% | ¼% | ½% |
|---|---|---|---|---|
| tensile strength (kN) | 0.486 | 0.865 | 0.841 | 0.670 |
| Stiffness (N/mm) | 1219 | 2329 | 1727 | 2161 |
| sample size | 5 | 4 | 4 | 1 |

Others working independently from us in our affiliated laboratory, the Center for Applied Energy Research, have measured a 25% increase in the failure stress of polystyrene that was augmented with a 1% addition of multi-walled carbon nanotubes. [Qian, 1999] Both preliminary sets of measurements strongly support the theoretical claims (made below) regarding the load transferring ability across the nanotube-matrix interface. [Qian, 1999] These data also provided the information that enabled subsequent sample size estimates.

If it is assumed that the nanotubes bond strongly to acrylic, then (for example, in tensile loading), classical micromechanical models for randomly oriented discontinuous fiber lamina can be applied to predict the modulus of the nanotube-acrylic composite. For varying concentrations of nanotubes, $V_{NT}$, the following equation predicts the composite tensile modulus $E_c$: [Mallick, 1993]

$$E_c = \left[ \frac{3}{8} \cdot \frac{1 + 2 \cdot (l_{NT}/d_{NT}) \cdot \eta_L \cdot V_{NT}}{1 - \eta_L \cdot V_{NT}} + \frac{5}{8} \cdot \frac{1 + 2 \cdot \eta_T \cdot V_{NT}}{1 - \eta_L \cdot V_{NT}} \right] \cdot E_{BC}$$

$$\eta_L = \frac{(E_{NT}/E_{BC}) - 1}{(E_{NT}/E_{BC}) + 2 \cdot (l_{NT}/d_{NT})}$$

$$\eta_L = \frac{(E_{NT}/E_{BC}) - 1}{(E_{NT}/E_{BC}) + 2}$$

where: $E_c$ represents tensile modulus of the nanotube-bone cement composite, $E_{BC}$ is the tensile modulus of dental acrylic (assumed to be approximately 2.5 GPa ([Lewis, 1997]), $E_{NT}$ is the tensile modulus of multi-walled nanotubes (assumed to be approximately 500 GPa ([Pan, 1999]), $V_{NT}$ is the volume fraction of nanotubes, and $l_{NT}$ the length, and $d_{NT}$ the outside diameter, of multi-walled nanotubes (our measurements suggest mean values for $d_{NT}$=30 nm and $l_{NT}$=50 μm).

The tensile modulus of the composite, $E_c$, as predicted from these equations, may be plotted as a function of carbon nanotube volume fraction $V_{NT}$ in a dental acrylic matrix. It is important to note that a 1% (0.01 on the graph) volume addition of the multi-walled nanotubes almost doubles the predicted tensile modulus.

The foregoing description of the preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. For example, it should be appreciated that the carbon nanotube augmented polymethylmethacrylate resin of the present invention may also be used as an injected biomaterial to prevent the collapse of severely osteoporotic vertebrae and femoral heads suffering from avascular necrosis. The augmented resin functions in this situation to support axial compressive loads to reduce pain and disability.

What is claimed is:

1. An augmented synthetic resin, comprising carbon nanotubes thoroughly disaggregated and uniformly dispersed in a polymethylmethacrylate matrix, said nanotubes having lengths between substantially 10–1000 nanometers and diameters between substantially 10–50 nanometers.

2. The synthetic resin of claim 1, wherein said carbon nanotubes are provided at a weight percentage of between substantially 0.005–5.0.

3. The synthetic resin of claim 2, wherein said carbon nanotubes have diameters between substantially 10–50 nanometers.

4. The synthetic resin of claim 1, wherein said carbon nanotubes are provided at a weight percentage of between substantially 0.15–2.0.

5. The synthetic resin of claim 4, wherein said carbon nanotubes have diameters between substantially 10–50 nanometers and lengths between substantially 10–1000 nanometers.

6. The synthetic resin of claim 5, wherein hollow spaces in said carbon nanotubes carry minute quantities of beneficial pharmaceutically effective compositions selected from a group consisting of antibiotics, anti-inflammatories, chemotherapeutic agents, bone growth promoting agents and any mixtures thereof.

7. The synthetic resin of claim 1, wherein said carbon nanotubes are multiwalled.

8. A dental restoration, comprising a body at least partially constructed from an augmented synthetic resin including carbon nanotubes dispersed in a biocompatible polymer of polymethylmethacrylate dissolved in a biocompatible reactive monomer of methylmethacrylate.

9. A method of preparing a synthetic resin, comprising:
mixing carbon nanotubes in a methylmethacrylate monomer;
disaggregating said carbon nanotubes;
adding polymethylmethacrylate polymer to the carbon nanotube-methylmethacrylate monomer mixture; and
vacuum mixing.

10. The method of preparing a synthetic resin of claim 9, wherein said disaggregating is completed by subjecting to ultrasonic agitation disaggregation or particle shearing.

11. A method of preparing a synthetic resin, comprising:
mixing carbon nanotubes with a solvent;
disaggregating said carbon nanotubes;
adding said disaggregated carbon nanotubes to a methylmethacrylate monomer and a polymethylmethacrylate polymer; and vacuum mixing.

12. The method of preparing a synthetic resin of claim 11, wherein said disaggregating is completed by subjecting to ultrasonic agitation disaggregation or particle shearing.

13. A method of preparing a synthetic resin, comprising:
mixing carbon nanotubes and polymethylmethacrylate polymer with a solvent;
disaggregating said carbon nanotubes;
separating the solvent from said disaggregated carbon nanotubes and polymethylmethacrylate polymer;
adding methylmethacrylate monomer; and
vacuum mixing.

14. The method of preparing a synthetic resin of claim 13, wherein said disaggregating is completed by subjecting to ultrasonic agitation disaggregation or particle shearing.

15. The synthetic resin of claim 1, wherein hollow spaces in said carbon nanotubes carry minute quantities of pharmaceutically effective compositions selected from a group consisting of antibiotics, anti-inflammatories, chemotherapeutic agents, bone growth promoting agents and any mixtures thereof.

* * * * *